United States Patent
Chockalingam

(10) Patent No.: US 8,236,988 B2
(45) Date of Patent: Aug. 7, 2012

(54) PREPARATION OF 2-(1,3-DIMETHYLBUTYL)ANILINE AND OTHER BRANCHED ALKYL-SUBSTITUTED-ANILINES

(75) Inventor: Kannappan Chockalingam, Baton Rouge, LA (US)

(73) Assignee: Albemarle Corporation, Baton Rouge, LA (US)

( * ) Notice: Subject to any disclaimer, the term of this patent is extended or adjusted under 35 U.S.C. 154(b) by 138 days.

(21) Appl. No.: 12/671,743

(22) PCT Filed: Aug. 1, 2008

(86) PCT No.: PCT/US2008/071877
§ 371 (c)(1),
(2), (4) Date: Feb. 2, 2010

(87) PCT Pub. No.: WO2009/029383
PCT Pub. Date: Mar. 5, 2009

(65) Prior Publication Data
US 2011/0237835 A1    Sep. 29, 2011

(51) Int. Cl.
*C07C 209/68* (2006.01)

(52) U.S. Cl. ........................................ 564/305; 564/409
(58) Field of Classification Search .................. 564/305, 564/409
See application file for complete search history.

(56) References Cited

U.S. PATENT DOCUMENTS

| 3,923,892 A | 12/1975 | Klopfer |
| 5,965,774 A | 10/1999 | Yoshikawa et al. |
| 7,105,565 B2 | 9/2006 | Walter |
| 2004/0116744 A1 | 6/2004 | Furuya et al. |
| 2006/0211771 A1 | 9/2006 | Elbe et al. |

FOREIGN PATENT DOCUMENTS

| GB | 1462254 | 1/1977 |
| JP | 05201934 | 8/1993 |
| WO | WO 2004/005242 | 1/2004 |

*Primary Examiner* — Peter G O Sullivan
(74) *Attorney, Agent, or Firm* — Marcy M. Hoelfling; Jeremy J. Kliebert; James A. Jubinsky

(57) ABSTRACT

Methods are provided for preparing branched alkyl-substituted-anilines, such as 2-(1,3-dimethylbutyl)aniline. Such methods comprise combining aniline, an alkyl-substituted-1-alkene, such as 4-methyl-i-pentene, and an aluminum alkyl catalyst.

5 Claims, No Drawings

PREPARATION OF 2-(1,3-DIMETHYLBUTYL)ANILINE AND OTHER BRANCHED ALKYL-SUBSTITUTED-ANILINES

BACKGROUND

It has long been desired to have efficient and economical processes for production of 2-(1,3-dimethylbutyl)aniline, which is useful, e.g., as an intermediate in agricultural applications.

U.S. Pat. No. 5,965,774 describes a three-step process for making 2-(1,3-dimethylbutyl)aniline. This method is disadvantageous in that three steps are required and the raw materials used are expensive. Additionally, the first process step is a Grignard reaction between isobutylmagnesium bromide and 2-aminoacetophenone, which is difficult to implement safely on commercial scale.

Similar processes are described in U.S. publication 2004/0116744 and U.S. Pat. No. 7,105,565 for 2-(1,4-dimethylpentyl)aniline and other substituted alkyl anilines. U.S. publication 2006/0211771 describes a method for making 2-(1,3-dimethylbutyl)aniline by reacting aniline and 4-methyl-1-pentene. These methods are also disadvantageous for use on a commercial scale. For example, undesired by-products are formed that are difficult to separate.

Thus, there is a need for commercially applicable processes for preparing 2-(1,3-dimethylbutyl)aniline and other branched alkyl-substituted-anilines.

THE INVENTION

This invention meets the above-described needs by providing methods for preparing branched alkyl-substituted-anilines, which methods comprise combining at least an aniline, an alkyl-substituted-1-alkene, and an aluminum alkyl. For example, a method according to this invention for preparing 2-(1,3-dimethylbutyl)aniline comprises combining at least an aniline, 4-methyl-1-pentene, and an aluminum alkyl. Such a method can be illustrated as follows:

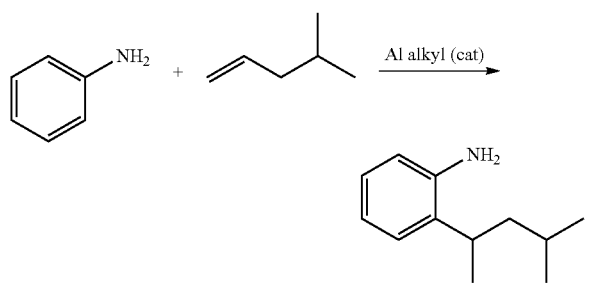

This invention also provides branched alkyl-substituted-anilines derived from at least an aniline, an alkyl-substituted-1-alkene, and an aluminum alkyl. For example, this invention provides 2-(1,3-dimethylbutyl)aniline derived from at least an aniline, 4-methyl-1-pentene, and an aluminum alkyl.

In this invention, the alkyl-substituted-1-alkene can be any suitable alkyl-substituted-1-alkene, as will be familiar to those skilled in the art given the teaching of this disclosure.

In this invention, the aluminum alkyl acts as a catalyst. Suitable aluminum alkyls include without limitation diethylaluminum chloride, ethylaluminum dichloride ethylaluminum sesquichloride, diisobutylaluminum chloride, ethylaluminum dichloride, isobutylaluminum dichloride, methylaluminum sesquichloride, and the like.

Processes according to this invention can be conducted at temperatures of about 200° C. to about 300° C., e.g., at temperatures of about 250° C. to about 270° C. The processes can be conducted at autogenous pressure, for example, the pressure can start at about 500 psig and end at about 100 psig. The processes can be conducted in an autoclave. The aluminum alkyl catalyst can be used in the range of 1 to 20 mol % based on aniline, for example, in the range of 5 to 10 mol %. The alkyl-substituted-1-alkene, e.g., 4-methyl-1-pentene, can be used in the range of 0.5 to 1.2 mol per mol of aniline, for example in the range is 0.6 to 0.75 mol per mol of aniline. The reaction that occurs can be allowed to proceed to about 60% aniline conversion in order to minimize formation of undesired by-products.

Methods of this invention are particularly advantageous in that they are one-step processes. Additionally, methods of this invention use a liquid catalyst, which is easy to handle. No solvent and diluents are necessary. Reaction work-up and product isolation are simple. Methods of this invention avoid using excess 4-methyl-1-pentene and eliminate the need to recycle.

EXAMPLES

The following examples are illustrative of the principles of this invention. It is understood that this invention is not limited to any one specific embodiment exemplified herein, whether in the examples or the remainder of this patent application.

Example 1

Aniline (210 g, 2.255 mol) was charged to a 1-L stainless steel Parr reactor. The reactor was sealed and flushed three times with 50 psig nitrogen. Aniline was stirred and ethylaluminum sesquichloride (39.9 g, 0.161 mol) was then added over 10 min. The mixture was heated to 150° C., held at this temperature for 30 minutes, and then cooled to ambient temperature. The pressure inside the reactor was vented and flushed one time with 50 psig of nitrogen. 4-Methyl-1-pentene (133.2 g, 1.583 mol) was added and the contents were heated to 260-265° C. The pressure inside the reactor reached about 400 psig at the maximum temperature. The mixture was allowed to stir at 260-262° C. for 17 hours and during this time the pressure gradually decreased to about 100 psig. Reactor contents were cooled to ambient temperature. Aqueous sodium hydroxide (25 wt % solution, 250 g) was added and the mixture was stirred for 10 min at 30 to 50° C. The mixture was allowed to separate and the aqueous phase (267 g) was removed. The organic phase (340 g) containing the crude product was analyzed to contain 27.4 wt % aniline and 44.2 wt % 2-(1,3-dimethylbutyl)aniline. Aniline conversion was found to be 55.6% and 2-(1,3-dimethylbutyl)aniline yield was found to be 37.6% based on aniline charged or 67.6% based on aniline reacted.

Example 2

Aniline (209.5 g, 2.25 mol) was treated with ethylaluminum sesquichloride (39.0 g, 0.158 mol) in the reactor as described in Example 1. 4-Methyl-1-pentene (190 g, 2.26 mol) was added and the mixture was held at 260-262° C. for 17 hours. Reactor contents were cooled to ambient temperature and treated with 25% aqueous sodium hydroxide solution. Aqueous phase was removed and the organic phase (388 g) was analyzed to contain 21.9 wt % aniline and 41.1 wt % 2-(1,3-dimethylbutyl)aniline. Aniline conversion was found to be 59.4% and 2-(1,3-dimethylbutyl)aniline yield was found to be 40% based on aniline charged or 67.3% based on aniline reacted. Crude product from this and from another similar experiment were combined and the total (767 g) was fractionally distilled at reduced pressure to give 290 g of pure 2-(1,3-dimethylbutyl)aniline (290 g, 36% yield based on aniline charged).

Example 3

Aniline (9.53 Kg, 102.33 mol) was charged to a 10-gallon INCONEL reactor and flushed three times with 25-30 psig of nitrogen. Ethylaluminum sesquichloride (1.85 Kg, 7.47 mol) was slowly added over a period of 15-30 min with stirring. Resulting mixture was heated and held at 150° C. for 30 min. Reactor was cooled to about 30° C. and the pressure inside was vented. 4-methyl-1-pentene (6.535 Kg, 77.65 mol) was charged, the contents were heated, and held at 265-270° C. for 17 h. During this time the pressure inside the reactor decreased from 470 to 110 psig. The reactor was cooled to ambient temperature and the reaction mixture was stirred with 10.02 Kg of 25 wt % aqueous sodium hydroxide solution. Layers were allowed to separate and the aqueous phase was removed. The organic phase (16.02 Kg) containing the crude product was analyzed to contain 24.35 wt % aniline and 43.37 wt % 2-(1,3-dimethylbutyl)aniline. Aniline conversion was found to be 59.1% and 2-(1,3-dimethylbutyl)aniline yield was found to be 38.3% based on aniline charged or 64.8% based on aniline reacted.

Example 4

Aniline (55.9 g, 0.6 mol) was charged to a 300-mL Parr reactor and treated with diethylaluminum chloride (7.2 g, 0.06 mol) at 150° C. for 30 min. The pressure was vented from the reactor and 4-methyl-1-pentene (55.5 g, 0.66 mol) was charged. The contents were heated to 300° C. and held at this temperature for 10 h. The reaction mixture was cooled to ambient temperature and treated with aqueous sodium hydroxide. The crude product was analyzed to contain 23.6 wt % aniline and 33.5 wt % 2-(1,3-dimethylbutyl)aniline. Aniline conversion was found to be 60.5% and 2-(1,3-dimethylbutyl)aniline yield was found to be 29.5% based on aniline charged or 48.8% based on aniline reacted.

It is to be understood that the reactants and components referred to by chemical name or formula anywhere in the specification or claims hereof, whether referred to in the singular or plural, are identified as they exist prior to being combined with or coming into contact with another substance referred to by chemical name or chemical type (e.g., another reactant, a solvent, or etc.). It matters not what chemical changes, transformations and/or reactions, if any, take place in the resulting combination or solution or reaction medium as such changes, transformations and/or reactions are the natural result of bringing the specified reactants and/or components together under the conditions called for pursuant to this disclosure. Thus the reactants and components are identified as ingredients to be brought together in connection with performing a desired chemical reaction or in forming a combination to be used in conducting a desired reaction. Accordingly, even though the claims hereinafter may refer to substances, components and/or ingredients in the present tense ("comprises", "is", etc.), the reference is to the substance, component or ingredient as it existed at the time just before it was first contacted, combined, blended or mixed with one or more other substances, components and/or ingredients in accordance with the present disclosure. Whatever transformations, if any, which occur in situ as a reaction is conducted is what the claim is intended to cover. Thus the fact that a substance, component or ingredient may have lost its original identity through a chemical reaction or transformation during the course of contacting, combining, blending or mixing operations, if conducted in accordance with this disclosure and with the application of common sense and the ordinary skill of a chemist, is thus wholly immaterial for an accurate understanding and appreciation of the true meaning and substance of this disclosure and the claims thereof. As will be familiar to those skilled in the art, the terms "combined", "combining", and the like as used herein mean that the components that are "combined" or that one is "combining" are put into a container with each other. Likewise a "combination" of components means the components having been put together in a container.

While the present invention has been described in terms of one or more preferred embodiments, it is to be understood that other modifications may be made without departing from the scope of the invention, which is set forth in the claims below.

What is claimed is:

1. A method for preparing a 2-(branched-alkyl-substituted)-aniline, comprising combining at least an aniline, an alkyl-substituted-1-alkene, and an aluminum alkyl catalyst.

2. A method for preparing 2-(1,3-dimethylbutyl)aniline comprising combining at least an aniline, 4-methyl-1-pentene, and an aluminum alkyl catalyst.

3. The method of claim 2 wherein the aluminum alkyl catalyst comprises diethylaluminum chloride.

4. The method of claim 2 wherein the aluminum alkyl catalyst comprises ethylaluminum sesquichloride.

5. A method for preparing 2-(1,3-dimethylbutyl)aniline comprising:

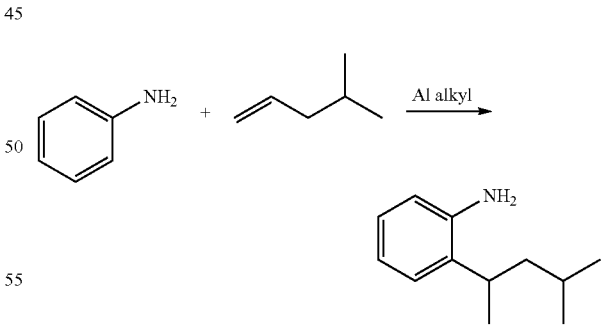

* * * * *